(12) United States Patent
Froggatt et al.

(10) Patent No.: US 7,115,287 B2
(45) Date of Patent: Oct. 3, 2006

(54) TOPICAL MEDICAMENT AND METHOD OF USE

(75) Inventors: John E. Froggatt, Elizabethton, TN (US); Susan E. Lyon, Gray, TN (US); Andrew S. May, Elizabethton, TN (US)

(73) Assignee: F.L.M., L.L.C., Elizabethton, TN (US)

( * ) Notice: Subject to any disclaimer, the term of this patent is extended or adjusted under 35 U.S.C. 154(b) by 0 days.

(21) Appl. No.: 11/070,981

(22) Filed: Mar. 3, 2005

(65) Prior Publication Data

US 2006/0198902 A1    Sep. 7, 2006

(51) Int. Cl.
*A61K 36/61* (2006.01)
(52) U.S. Cl. .................. 424/769; 424/642; 514/725; 514/167; 514/458; 514/169
(58) Field of Classification Search .................. None
See application file for complete search history.

(56) References Cited

U.S. PATENT DOCUMENTS

| | | | | |
|---|---|---|---|---|
| 4,160,844 A | * | 7/1979 | Orr et al. ............... | 514/455 |
| 5,849,729 A | * | 12/1998 | Zoumas et al. ............ | 514/169 |
| 6,114,389 A | * | 9/2000 | Bouras .................. | 514/574 |
| 6,599,513 B1 | | 7/2003 | Deckers et al. | |
| 2004/0096410 A1 | | 5/2004 | Maley et al. | |
| 2004/0185123 A1 | * | 9/2004 | Mazzio et al. ............ | 424/730 |

FOREIGN PATENT DOCUMENTS

| | | |
|---|---|---|
| DE | 10161729 | 6/2003 |
| JP | 2002-212053 | 7/2002 |
| JP | 2002-326922 | 11/2002 |
| WO | WO 93/25213 | 12/1993 |

* cited by examiner

*Primary Examiner*—Susan D. Coe
(74) *Attorney, Agent, or Firm*—Gable and Gotwals

(57) ABSTRACT

A topical medicament, and associate method of use, for the treatment of dermatologic conditions in both humans and animals is provided. The medicament includes a mixture of Vitamin A, Vitamin D, Vitamin E, lanolin, petroleum jelly, colloidal silver, ti tree oil, zinc oxide and corn starch in appropriate proportions. Ingredient proportions may be varied to form an ointment or a paste having a thicker consistency than the ointment.

15 Claims, No Drawings

TOPICAL MEDICAMENT AND METHOD OF USE

1. FIELD OF THE INVENTION

The present invention relates generally to a topical medicament for the treatment of dermatologic conditions. More particularly, the invention relates to a topical medicament that uses natural ingredients to correct dermatologic conditions of varying causes and degree of tissue destruction while protecting the area from further degradation.

2. BACKGROUND OF THE INVENTION

The skin of humans and animals is subject to a variety of undesirable dermatologic conditions, including excoriation (chaffing), yeast/fungal infections, thermal and friction burns, acne, poison ivy, psoriasis, rashes, skin abrasions, decubitii, diaper rash, dermatitis, puncture wounds such as dog bites, and others. Numerous types and compositions of ointments are available for the treatment of such dermatologic conditions. Unfortunately, many of the ointments available today lack the desired healing effect, and many that do exhibit a desired healing effect also exhibit one or more undesired side effects. For example, corticosteroids and salicylic acid are often employed in the treatment of psoriasis with less than desirable results, and irreversible skin aging (atrophy) often results from the use of ointments containing cortisone. Additionally, many of the currently available topical ointments are condition specific and ineffective in treating multiple dermatologic conditions.

What is needed, therefore, is a topical medicament that provides desired healing effects for multiple dermatologic conditions.

BRIEF SUMMARY OF THE INVENTION

The present invention achieves its objectives by providing a topical medicament in either ointment or paste form. The medicament, effective in treating dermatologic conditions, is a mixture of Vitamin A oil, Vitamin D oil, Vitamin E oil, lanolin, petroleum jelly, colloidal silver, ti tree oil, zinc oxide and corn starch in appropriate proportions. In a preferred embodiment, an ointment is provided according to the following formulation:
   a) about 1.5 ml of Vitamin A oil;
   b) about 0.5 ml of Vitamin D oil;
   c) about 2.0 ml of Vitamin E oil;
   d) about 30 g of lanolin;
   e) about 45 g of petroleum jelly;
   f) about 2 ml of 10 ppm colloidal silver solution;
   g) about 1 ml of ti tree oil;
   h) about 15 g of zinc oxide; and
   i) about 6 g of corn starch.

The medicament is provided in paste form according to the following formulation:
   a) about 1.5 ml of Vitamin A oil;
   b) about 0.5 ml of Vitamin D oil;
   c) about 2.0 ml of Vitamin E oil;
   d) about 30 g of lanolin;
   e) about 45 g of petroleum jelly;
   f) about 2 ml of 10 ppm colloidal silver solution;
   g) about 1 ml of ti tree oil;
   h) about 30 g of zinc oxide; and
   i) about 12 g of corn starch.

Dermatologic conditions treatable by the medicament include, but are not limited to, excoriation, psoriasis, yeast infection, fungal infection, bacterial infection, burn, acne, poison ivy, rash, lesion, abrasion, decubitus, diaper rash, dermatitis, bites, stings and puncture wounds.

In use, the medicament is to be applied to the affected tissue twice daily. The affected tissue should be washed with warm water and soap, and then dried prior to applying the medicament in a small amount, using a circular motion until fully absorbed.

DETAILED DESCRIPTION OF THE PREFERRED EMBODIMENT(S)

In the preferred embodiment of the invention, all natural ingredients are mixed into a topical medicament for use in correcting dermatologic conditions of varying causes and degree of tissue destruction while protecting the affected tissue from further degradation. The medicament has been found to be effective in treating dermatologic conditions of both humans and animals. Specific dermatologic conditions for which the medicament has been found to be effective in treating include excoriation (chaffing), psoriasis, yeast infection, fungal infection, bacterial infection, burns, acne, poison ivy, rashes, lesions, abrasions, decubitii, diaper rash, dermatitis, bites, stings and puncture wounds.

The ingredients can be mixed in varying proportions to form an ointment or a paste having a thicker consistency than the ointment. Following is a preferred formula of the topical medicament in ointment form:
   a) about 1.5 ml of Vitamin A oil;
   b) about 0.5 ml of Vitamin D oil;
   c) about 2.0 ml of Vitamin E oil;
   d) about 30 g of lanolin;
   e) about 45 g of petroleum jelly;
   f) about 2 ml of 10 ppm colloidal silver solution;
   g) about 1 ml of ti tree oil;
   h) about 15 g of zinc oxide; and
   i) about 6 g of corn starch.

The above formulation for ointment yields about 120 ml of medicament.

In paste form, the amounts of zinc oxide and corn starch are doubled to yield the following formula:
   a) about 1.5 ml of Vitamin A oil;
   b) about 0.5 ml of Vitamin D oil;
   c) about 2.0 ml of Vitamin E oil;
   d) about 30 g of lanolin;
   e) about 45 g of petroleum jelly;
   f) about 2 ml of 10 ppm colloidal silver solution;
   g) about 1 ml of ti tree oil;
   h) about 30 g of zinc oxide; and
   i) about 12 g of corn starch.

Testing of the medicament has shown that each ingredient in the above stated formulations can be varied by about −10% to +10% with the same healing effects noted.

The above ingredients, as further described below, have been found to promote rapid repair of affected tissue and, by the action they perform, can be deemed anti-microbial. These ingredients are all natural in composition with medicinal properties that promote tissue repair and healing, along with certain astringent properties. The medicament also provides a moisture barrier of considerable efficacy, which protects the affected tissue from further degradation during the healing process. The ingredients were selected for their catalistic behavior in stimulating regeneration of new tissue growth, thereby quickly closing the wound and further reducing pathogenic invasion. Along with rapid healing, there is minimal, if any, eschar formation.

VITAMIN A (Retinol) is found in green and yellow leafy vegetables, egg yolk, and fish liver oil. It is often referred to as an "anti-infective" vitamin and is useful in treating skin disorders such as psoriasis and acne. Retinol has a natural anti-oxidant effect and thereby acts as a barrier to assist in keeping body surfaces healthy. (P D R Medical Dictionary, $2^{nd}$ ed.)

VITAMIN D (Cholecalciferol), an anti-oxidant, is found in cod liver oil. It is absorbable through the skin and enhances calcium absorption, thereby promoting healing. It is recognized that the Eskimo, through their consumption of fish oils, have fewer dermatologic problems. (P D R Medical Dictionary, $2^{nd}$ ed.)

VITAMIN E (Tocopherol) is also found in green and yellow leafy vegetables, egg yolk, and fish oil. It is a protagonist for Vitamin A, and being directly absorbable through the skin, is a stimulant for new cell growth. (P D R Medical Dictionary, $2^{nd}$ ed.)

LANOLIN, a fat, is a derivative of wool and used as a base for the medicament. In the above formulations, it is used as a moisture barrier and skin softener. The waxy matrix of lanolin, when mixed with petroleum jelly, creates the basis of the barrier protection of this medicament.

PETROLEUM JELLY is a yellowish mixture of the softer members of the paraffin or methane series of hydrocarbons. It is obtained from petroleum as an intermediate product of the distillation process and used as a base for the above medicament. Petroleum jelly is a mixture of hydro-carbons found in the earth—believed to be from fossilized animal and plant remains. In the above formulations, it compliments the other oils in creating a smoother mixture.

COLLOIDAL SILVER is an aggregation of atoms and/or molecules in a finely divided state, dispersed in a liquid medium. It is a suspension of submicroscopic metallic silver particles in a colloidal base, such as demineralized water. It resists sedimentation, diffusion and filtration, thus differing from precipitates. It is a gluelike, yellowish, translucent homogenous material. In the preferred formulations described herein, the colloidal silver is present in solution in a concentration of about 10 ppm. It has the advantageous effect of killing bacteria and viruses that may be present on or in the affected tissue. Thus, it functions in the above formulations as an all natural antibiotic. (P D R Medical Dictionary, $2^{nd}$ ed.)

TI TREE OIL (*Melaleuca Alternifolia*), which is obtained from the leaves of the ti tree found in Australia, is employed for its antiseptic and anti-fungal properties. It acts as a skin disinfectant which promotes a more rapid skin/tissue repair and a good environment for re-growth. As a skin disinfectant, it has an efficacy against a wide range of organisms, including most strains of p. acne. In the preferred formulations described herein, the oil is 100% pure. (Encyclopedia of Natural Medicine, Rev. $2^{nd}$ ed., Michael T. Murray)

ZINC OXIDE (ZnO) is used as a protective in the above formulations. It promotes wound healing/tissue regeneration. Normal preparation is 20% ZnO in mineral oil or a white petrolatum base, used as a local surfactant for varying skin conditions. Absorption of ZnO helps the body to utilize Vitamin A in the above formulations. (P D R Medical Dictionary, $2^{nd}$ ed.)

CORN STARCH is obtained from the endosperm of corn. It is used as a thickening agent, thereby increasing the viscosity of the above formulations. It is also a natural sponge for body fluids such as exudates.

From the above, it will be appreciated that each ingredient in the medicament synergistically assists the others to attain the desired effects. Additional ingredients that adversely affect this synergism constitute a material change in the above formulations and are, therefore, not recommended.

Application and use of the medicament is essentially the same for all treatable dermatologic conditions of both humans and animals. Twice daily, the affected tissue is washed with warm water and soap, and then dried. The medicament is then applied to the affected tissue in an amount sufficient to promote healing. Preferably, the medicament is applied by using a circular motion to rub the medicament into the skin until fully absorbed. If there is a presence of stool or urine due to incontinence, gently cleanse, then again wash and repeat the procedure. Do this twice daily, preferably 12 hours apart. Since this is a barrier solution, it is unnecessary to apply more than can/will be absorbed.

For those with a decubitus ulceration, the above method of use applies. However, a rubber glove or finger cot should be used to rub the medicament into the tissue. At the onset, if desired, one may apply the medicament to a small piece of gauze being certain that when applied complete tissue contact is made. Cover with a non-adhering dressing.

It has been repeatedly observed that the moisture barrier remains intact when the treated tissue is gently cleansed, such as is usually necessary when an incontenant accident occurs. There is usually a slight tingling sensation experienced following the first two or three applications of the medicament, then this sensation dissipates. Notable tissue improvements are commonly observed following the second application.

Gender, age, and nutritional level have been shown to be inconsequential in the healing rate. Essentially all involved with the test subjects have been impressed with the rapidity of wound closure for decubitus ulcerations. The one exception was a 76 year old male subject with a stage three decubitus ulcer and a nutrition level of one, who had a 13-day healing period.

Tables 1–7 are examples of test subject response (on both humans and animals) to the medicament in which the medicament was applied to the affected tissue twice daily. The test samples of the medicament were combined by hand, in a ceramic bowl. Using a spoon, they were blended in a folding manner incorporating both dry and wet ingredients creating an emulsion. Once accomplished, it was then vigorously hand whipped creating a light, aerated creamy mixture. This formula set forth above was used to make about 120 ml of product. For each table, the subject's level of nutrition, skin condition, and observed response are indicated numerically accordingly to the following:

| Level of Nutrition | Skin Condition (Stage/Degree) | Observed Response |
|---|---|---|
| 1. emaciated, poor skin turgor | 1. reddened skin | 1. no change |
| 2. hydrated, fair skin turgor | 2. reddened, swollen, "scald" | 2. a little change, no further improvement |
| 3. hydrated, good skin turgor | 3. excoriated | 3. moderate change, no further improvement |
|  | 4. excoriated and weeping | 4. good improvement, back to normal |
|  | 5. open ulcer | 5. complete improvement, skin normal |

TABLE 1

Response to Medicament Applications, Twice Daily, Assorted Conditions, Female Participants

| Age | Level of Nutrition | Area | Causative Agent | Stage/ Degree | Improvement Time In Days | Response |
|---|---|---|---|---|---|---|
| 1 | 3 | Arms | Contact Derm. | 2 | 2 | 5 |
| 16 | 3 | Face | Acne | 2 | 3 | 5 |
| 48 | 3 | Hands | Psoriasis | 2 | 5 | 5 |
| 51 | 3 | Hands/ Arms | Contact Derm. | 1 | 3 | 5 |
| 60 | 3 | Buttocks | Shingles | 3 | 5 | 4 |
| 61 | 3 | Hands/ Arms | Contact Derm. | 2 | 3 | 5 |
| 64 | 2 | Face | Rash Unk. Cause | 3 | 4 | 5 |

TABLE 2

Response to Medicament Applications, Twice Daily, Assorted Conditions, Male Participants

| Age | Level of Nutrition | Area | Causative Agent | Stage/ Degree | Improvement Time In Days | Response |
|---|---|---|---|---|---|---|
| 12 | 3 | L Arm/Leg | Yellow Jacket | 2 | 1 | 5 |
| 24 | 3 | Arms | Contact Derm. | 2 | 2 | 5 |
| 36 | 3 | Arms | Contact Derm. | 2 | 2 | 5 |
| 52 | 3 | L Arm | Yellow Jacket | 1 | 1.5 | 5 |
| 60 | 3 | L Hand | Infected wart | 3 | 3 | 4 |
| 69 | 3 | Face L Cheek | Dog Scratch | 2 | 2 | 5 |
| 70 | 3 | L Hand | Yellow Jacket | 2 | 2 | 5 |
| 70 | 3 | L Hand | Steam Burn | 1 | 1 | 5 |

TABLE 3

Response to Medicament Applications, Twice Daily, Decubitus Ulcer, Female Participants

| Age | Level of Nutrition | Area | Causative Agent | Stage/ Degree | Improvement Time In Days | Response |
|---|---|---|---|---|---|---|
| 56 | 2 | R Elbow | Pressure | 1 | 3.5 | 5 |
| 76 | 1 | R Hip | Pressure | 5 | 3 | 4 |
| 82 | 1 | Saccrum | Pressure | 5 | 7 | 4 |
| 90 | 2 | Saccrum | Pressure | 2 | 5 | 5 |

TABLE 4

Response to Medicament Applications, Twice Daily, Decubitus Ulcer, Male Participants

| Age | Level of Nutrition | Area | Causative Agent | Stage/ Degree | Improvement Time In Days | Response |
|---|---|---|---|---|---|---|
| 46 | 2 | R Hip | Pressure | 2 | 5 | 4 |
| 76 | 1 | Saccrum | Pressure | 2 | 13 | 4 |
| 82 | 3 | R Buttock | Pressure | 2 | 5 | 5 |
| 88 | 3 | R Hip | Pressure | 2 | 5 | 4 |

TABLE 5

Response to Medicament Applications, Twice Daily, Yeast Infection, Female Participants

| Age | Level of Nutrition | Area | Causative Agent | Stage/ Degree | Improvement Time In Days | Response |
|---|---|---|---|---|---|---|
| 58 | 1 | Breasts Penniculus | Yeast | 1 | 2.5 | 5 |
| 62 | 3 | Breasts Penniculus | Yeast | 1 | 3 | 5 |

TABLE 5-continued

Response to Medicament Applications, Twice Daily, Yeast Infection, Female Participants

| Age | Level of Nutrition | Area | Causative Agent | Stage/ Degree | Improvement Time In Days | Response |
|---|---|---|---|---|---|---|
| 62 | 3 | Groin | Yeast | 2 | 5 | 5 |
| 76 | 1 | Breasts | Yeast | 3 | 3.5 | 5 |
| 81 | 2 | Buttocks Anus | Yeast | 3 | 3 | 4 |
| 88 | 2 | Buttocks Anus | Yeast | 4 | 5 | 5 |
| 92 | 2 | Buttocks Anus | Yeast | 3 | 6 | 5 |
| 92 | 2 | Breasts | Yeast | 3 | 4 | 5 |

TABLE 6

Response to Medicament Applications, Twice Daily, Yeast Infection, Male Participants

| Age | Level of Nutrition | Area | Causative Agent | Stage/ Degree | Improvement Time In Days | Response |
|---|---|---|---|---|---|---|
| 45 | 3 | Buttocks | Yeast | 1 | 2 | 5 |
| 47 | 1 | R. Elbow | Yeast | 4 | 3 | 4 |
| 54 | 3 | Penniculus Anus | Yeast | 1 | 4 | 5 |
| 62 | 1 | Buttocks Anus | Yeast | 3 | 4 | 5 |
| 71 | 2 | Buttocks Anus | Yeast | 3 | 3 | 5 |
| 72 | 2 | Buttocks | Yeast | 4 | 6 | 5 |
|  | 3 | Hands Anus | Yeast | 3 | 5 | 2 |
| 80 | 3 | Buttocks | Yeast | 4 | 6 | 4 |
| 86 | 3 | Groin | Yeast | 3 | 3 | 5 |
| 89 | 2 | Groin | Yeast | 2 | 3 | 5 |

TABLE 7

Response to Medicament Applications, Twice Daily, Assorted Conditions, Animals

| Age | Level of Nutrition | Area | Causative Agent | Stage/ Degree | Improvement Time In Days | Response |
|---|---|---|---|---|---|---|
| 3 | 3 | Croup | Gnawed due to Fleas/Allergy | 4 | 3 | 5 (Dog) |
| 5 | 3 | L. Shoulder | Infected Horse Bite Purulent | 4 | 3 | 5 (Horse) |

The foregoing description details certain preferred embodiments of the present invention and describes the best mode contemplated. It will be appreciated, however, that the ingredients, their preparation, and their use and the advantages thereof will be apparent to those skilled in the art of wound care. Changes may be made in the details of the preparation and the configuration of the ingredients without departing from the spirit and scope of the disclosure. Therefore, the description provided herein is to be considered exemplary, rather than limiting, and the true scope of the medicament is that defined by the following claims and the full range of equivalency to which each element thereof is entitled.

What is claimed is:

1. A topical medicament for treating a dermatologic condition, the medicament comprising:
   a) Vitamin A oil;
   b) Vitamin D oil;
   c) Vitamin E oil;
   d) lanolin;
   e) petroleum jelly;
   f) colloidal silver;
   g) ti tree oil;
   h) zinc oxide; and
   i) corn starch.

2. The medicament of claim 1, wherein the medicament is the form of an ointment including:
   a) about 1.5 ml of Vitamin A oil;
   b) about 0.5 ml of Vitamin D oil;
   c) about 2.0 ml of Vitamin E oil;
   d) about 30 g of lanolin;
   e) about 45 g of petroleum jelly;
   f) about 2 ml of 10 ppm colloidal silver solution;
   g) about 1 ml of ti tree oil;
   h) about 15 g of zinc oxide; and
   i) about 6 g of corn starch.

3. The medicament of claim 1, wherein the medicament is the form of a paste including:
   a) about 1.5 ml of Vitamin A oil;
   b) about 0.5 ml of Vitamin D oil;
   c) about 2.0 ml of Vitamin E oil;
   d) about 30 g of lanolin;
   e) about 45 g of petroleum jelly;
   f) about 2 ml of 10 ppm colloidal silver solution;
   g) about 1 ml of ti tree oil;
   h) about 30 g of zinc oxide; and
   i) about 12 g of corn starch.

4. The medicament of claim 1, wherein said dermatologic condition includes one or more dermatologic conditions selected from the group consisting of excoriation, psoriasis, yeast infection, fungal infection, bacterial infection, burn, acne, poison ivy, rash, lesion, abrasion, decubitus, diaper rash, dermatitis, bites, stings and puncture wound.

5. A method for treating a dermatologic condition, the method comprising applying in a circular motion to tissue affected by a dermatologic condition a therapeutically effective amount of the medicament described in claim 1.

6. The method of claim 5, further comprising the steps of:
   washing the tissue affected by the dermatologic condition with water and soap; and
   drying the tissue affected by the dermatologic condition; prior to applying the medicament.

7. The method of claim 6, wherein said washing, drying, and applying steps are performed twice daily.

8. A topical medicament for treating a dermatologic condition, the medicament comprising:
   a) about 1.5 ml of Vitamin A oil;
   b) about 0.5 ml of Vitamin D oil;
   c) about 2.0 ml of Vitamin E oil;
   d) about 30 g of lanolin;
   e) about 45 g of petroleum jelly;
   f) about 2 ml of 10 ppm colloidal silver solution;
   g) about 1 ml of ti tree oil;
   h) about 15 g of zinc oxide; and
   i) about 6 g of corn starch.

9. The medicament of claim 8, wherein said dermatologic condition includes one or more dermatologic conditions selected from the group consisting of excoriation, psoriasis, yeast infection, fungal infection, bacterial infection, burn, acne, poison ivy, rash, lesion, abrasion, decubitus, diaper rash, dermatitis, bites, stings and puncture wound.

10. A method for treating a dermatologic condition, the method comprising applying in a circular motion to tissue affected by a dermatologic condition a therapeutically effective amount of the medicament described in claim 8.

11. The method of claim 10, further comprising the steps of:
    washing the tissue affected by the dermatologic condition with water and soap; and
    drying the tissue affected by the dermatologic condition; prior to applying the medicament.

12. A topical medicament for treating a dermatologic condition, the medicament consisting of:
    a) Vitamin A oil;
    b) Vitamin D oil;
    c) Vitamin E oil;
    d) lanolin;
    e) petroleum jelly;
    f) colloidal silver;
    g) ti tree oil;
    h) zinc oxide; and
    i) corn starch.

13. The medicament of claim 12, wherein the medicament further consists of:
    a) about 1.5 ml of Vitamin A oil;
    b) about 0.5 ml of Vitamin D oil;
    c) about 2.0 ml of Vitamin E oil;
    d) about 30 g of lanolin;
    e) about 45 g of petroleum jelly;
    f) about 2 ml of 10 ppm colloidal silver solution;
    g) about 1 ml of ti tree oil;
    h) about 15 g of zinc oxide; and
    i) about 6 g of corn starch.

14. A method for treating a dermatologic condition, the method consisting of applying to tissue affected by a dermatologic condition an effective amount of the medicament described in claim 12.

15. A topical medicament for treating a dermatologic condition, the medicament consisting essentially of:
    a) Vitamin A oil;
    b) Vitamin D oil;
    c) Vitamin E oil;
    d) lanolin;
    e) petroleum jelly;
    f) colloidal silver;
    g) ti tree oil;
    h) zinc oxide; and
    i) corn starch.

* * * * *

UNITED STATES PATENT AND TRADEMARK OFFICE
CERTIFICATE OF CORRECTION

| | | |
|---|---|---|
| PATENT NO. | : 7,115,287 B2 | Page 1 of 1 |
| APPLICATION NO. | : 11/070981 | |
| DATED | : October 3, 2006 | |
| INVENTOR(S) | : John E. Froggatt, Susan E. Lyon and Andrew S. May | |

It is certified that error appears in the above-identified patent and that said Letters Patent is hereby corrected as shown below:

On the Title Page, In the ABSTRACT, line 5, "colloidal silver" should be changed to --silver hydrosol--

Column 1, lines 51 and 62, "colloidal silver" for each occurrence, should be changed to --silver hydrosol--

Column 2, lines 34 and 48, "colloidal silver" for each occurrence, should be changed to --silver hydrosol--

Column 3, line 32, "COLLOIDAL SILVER" should be changed to --SILVER HYDROSOL--

Column 3, line 39, "colloidal silver" should be changed to --silver hydrosol--

Column 3, line 43-44, delete "(P D R Medical Dictionary, 2nd ed.)"

Column 8, line 63, "colloidal silver" should be changed to --silver hydrosol--

Column 9, lines 8 and 36, "colloidal silver" for each occurrence, should be changed to --silver hydrosol--

Column 10, lines 16, 27 and 42, "colloidal silver" for each occurrence, should be changed to --silver hydrosol--

Signed and Sealed this
Fourth Day of September, 2012

David J. Kappos
*Director of the United States Patent and Trademark Office*